(12) United States Patent
Glukhovsky et al.

(10) Patent No.: US 7,996,067 B2
(45) Date of Patent: Aug. 9, 2011

(54) IN-VIVO IMAGING DEVICE, OPTICAL SYSTEM AND METHOD

(75) Inventors: Arkady Glukhovsky, Santa Clarita, CA (US); Gavriel Meron, Petach Tikva (IL); Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 725 days.

(21) Appl. No.: 10/879,483

(22) Filed: Jun. 30, 2004

(65) Prior Publication Data

US 2005/0068416 A1    Mar. 31, 2005
US 2008/0055404 A9    Mar. 6, 2008

Related U.S. Application Data

(63) Continuation-in-part of application No. 10/879,276, filed on Jun. 30, 2004, now Pat. No. 6,934,093, which is a continuation-in-part of application No. 10/009,837, filed as application No. PCT/IL00/00349 on Jun. 15, 2000, now Pat. No. 6,836,377, said application No. 10/879,483 is a continuation-in-part of application No. 10/478,252, filed as application No. PCT/IL02/00391 on May 20, 2002, now abandoned.

(30) Foreign Application Priority Data

Jun. 15, 1999    (IL) .......................................... 130486
May 20, 2001    (IL) .......................................... 143258

(51) Int. Cl.
*A61B 6/00* (2006.01)
*A61B 1/06* (2006.01)

(52) U.S. Cl. ...................................... 600/476; 600/160

(58) Field of Classification Search .................. 600/476, 600/160, 176
See application file for complete search history.

(56) References Cited

U.S. PATENT DOCUMENTS

| | | |
|---|---|---|
| 3,289,779 A | 12/1966 | Feucht |
| 3,683,389 A | 8/1972 | Hollis |
| 3,745,325 A | 7/1973 | Harvey |
| 3,971,362 A | 7/1976 | Pope et al. |
| 4,005,287 A | 1/1977 | Cook |

(Continued)

FOREIGN PATENT DOCUMENTS

DE    323 006 C    7/1920

(Continued)

OTHER PUBLICATIONS

U.S. Appl. No. 11/221,841, filed Sep. 9, 2005, Glukhovsky, Arkady.

(Continued)

*Primary Examiner* — Tse Chen
*Assistant Examiner* — Jacqueline Cheng
(74) *Attorney, Agent, or Firm* — Pearl Cohen Zedek Latzer, LLP

(57) ABSTRACT

An in-vivo device may include an optical system, and a method for viewing in-vivo sites. A dome or cover may cover an end of the device, protecting optical elements such as illumination devices or imagers, which may be behind the dome. The dome may be forward projecting. The field of view of the imager may be for example forward looking. Illumination element(s) and a receiving unit or imager may be disposed behind a single optical window, which for example may enable obtaining of images free of backscatter and stray light.

21 Claims, 8 Drawing Sheets

U.S. PATENT DOCUMENTS

| | | | |
|---|---|---|---|
| 4,017,163 A | | 4/1977 | Glass |
| 4,027,510 A | | 6/1977 | Hiltebrandt |
| 4,177,800 A | | 12/1979 | Enger |
| 4,198,960 A | | 4/1980 | Utsugi |
| 4,217,045 A | | 8/1980 | Ziskind |
| 4,234,912 A | | 11/1980 | Barnes et al. |
| 4,239,040 A | | 12/1980 | Hosoya et al. |
| 4,278,077 A | | 7/1981 | Mizumoto |
| 4,439,197 A | | 3/1984 | Honda et al. |
| 4,491,865 A | | 1/1985 | Danna et al. |
| 4,596,050 A | | 6/1986 | Rogers |
| 4,646,724 A | | 3/1987 | Sato et al. |
| 4,689,621 A | | 8/1987 | Kleinberg |
| 4,735,214 A | | 4/1988 | Berman |
| 4,741,327 A | | 5/1988 | Yabe |
| 4,819,620 A | | 4/1989 | Okutsu |
| 4,844,076 A | | 7/1989 | Lesho et al. |
| 4,917,097 A | | 4/1990 | Proudian et al. |
| 4,936,823 A | | 6/1990 | Colvin et al. |
| 4,951,135 A | | 8/1990 | Sasagawa et al. |
| 5,010,412 A | | 4/1991 | Garriss |
| 5,042,486 A | | 8/1991 | Pfeiler et al. |
| 5,166,787 A | | 11/1992 | Irion |
| 5,187,572 A | | 2/1993 | Nakamura et al. |
| 5,217,449 A | | 6/1993 | Yuda et al. |
| 5,222,477 A | | 6/1993 | Lia |
| 5,267,033 A | | 11/1993 | Hoshino |
| 5,279,607 A | | 1/1994 | Schentag et al. |
| 5,335,662 A | | 8/1994 | Kimura et al. |
| 5,368,027 A | | 11/1994 | Lubbers et al. |
| 5,373,840 A | | 12/1994 | Knighton |
| 5,395,366 A | | 3/1995 | D'Andrea et al. |
| 5,429,132 A | | 7/1995 | Guy et al. |
| 5,489,256 A | * | 2/1996 | Adair ................ 600/133 |
| 5,495,114 A | | 2/1996 | Adair |
| 5,603,687 A | | 2/1997 | Hori et al. |
| 5,604,531 A | * | 2/1997 | Iddan et al. ............ 348/76 |
| 5,653,677 A | | 8/1997 | Okada et al. |
| 5,662,587 A | | 9/1997 | Grundfest et al. |
| 5,681,260 A | * | 10/1997 | Ueda et al. ............ 600/114 |
| 5,697,384 A | | 12/1997 | Miyawaki et al. |
| 5,718,663 A | | 2/1998 | Wulfsberg |
| 5,745,833 A | | 4/1998 | Abe et al. |
| 5,764,274 A | | 6/1998 | Sousa et al. |
| 5,819,736 A | | 10/1998 | Avny et al. |
| 5,833,603 A | * | 11/1998 | Kovacs et al. ............ 600/317 |
| 5,840,014 A | | 11/1998 | Miyano et al. |
| 5,993,378 A | | 11/1999 | Lemelson |
| 6,240,312 B1 | * | 5/2001 | Alfano et al. ............ 600/476 |
| 6,416,181 B1 | | 7/2002 | Kessler et al. |
| 6,428,469 B1 | | 8/2002 | Iddan et al. |
| 6,511,182 B1 | | 1/2003 | Agostinelli et al. |
| 6,612,701 B2 | | 9/2003 | Westort et al. |
| 6,632,171 B2 | | 10/2003 | Iddan et al. |
| 6,632,175 B1 | | 10/2003 | Marshall et al. |
| 6,709,387 B1 | | 3/2004 | Glukhovsky et al. |
| 6,764,440 B2 | | 7/2004 | Iddan et al. |
| 6,836,377 B1 | | 12/2004 | Kislev et al. |
| 6,918,872 B2 | | 7/2005 | Yokoi et al. |
| 6,934,093 B2 | | 8/2005 | Kislev et al. |
| 6,984,205 B2 | | 1/2006 | Gazdzinski |
| 7,009,634 B2 | * | 3/2006 | Iddan et al. ............ 348/76 |
| 7,327,525 B2 | | 2/2008 | Kislev et al. |
| 2001/0017649 A1 | | 8/2001 | Yaron |
| 2001/0035902 A1 | | 11/2001 | Iddan et al. |
| 2001/0051766 A1 | | 12/2001 | Gazdzinski |
| 2002/0103417 A1 | | 8/2002 | Gazdzinski |
| 2002/0198439 A1 | | 12/2002 | Mizuno |
| 2003/0018280 A1 | | 1/2003 | Lewkowicz et al. |
| 2003/0020810 A1 | | 1/2003 | Takizawa et al. |
| 2003/0085994 A1 | | 5/2003 | Fujita et al. |
| 2003/0139647 A1 | | 7/2003 | Raz et al. |
| 2003/0158503 A1 | | 8/2003 | Matsumoto |
| 2003/0167000 A1 | * | 9/2003 | Mullick et al. ............ 600/424 |
| 2003/0171648 A1 | | 9/2003 | Yokoi et al. |
| 2003/0171649 A1 | | 9/2003 | Yokoi et al. |
| 2003/0171652 A1 | | 9/2003 | Yokoi et al. |
| 2003/0208107 A1 | | 11/2003 | Refael |
| 2004/0073087 A1 | | 4/2004 | Glukhovsky et al. |
| 2004/0171914 A1 | | 9/2004 | Avni |
| 2005/0068416 A1 | | 3/2005 | Glukhovsky et al. |
| 2005/0185299 A1 | | 8/2005 | Kislev et al. |
| 2007/0002135 A1 | | 1/2007 | Glukhovsky |

FOREIGN PATENT DOCUMENTS

| | | | |
|---|---|---|---|
| DE | | 2929429 | 2/1980 |
| DE | | 34 40 177 | 5/1986 |
| DE | | 3928515 | 6/1990 |
| DE | | 9016829 | 2/1991 |
| EP | | 0667115 | 8/1995 |
| EP | | 0677272 | 10/1995 |
| EP | | 0941 691 | 9/1999 |
| FR | | 2723215 | 2/1996 |
| GB | | 2291980 | 2/1996 |
| JP | | 57-45833 | 3/1982 |
| JP | | 63-200115 | 8/1988 |
| JP | | 6142081 | 5/1991 |
| JP | | 3264037 | 11/1991 |
| JP | | 3289779 | 12/1991 |
| JP | | 4109927 | 4/1992 |
| JP | | 04109927 A | * 4/1992 |
| JP | | 04-144533 | 5/1992 |
| JP | | 1992-144533 | 5/1992 |
| JP | | 4180736 | 6/1992 |
| JP | | 5015515 | 1/1993 |
| JP | | 6063051 | 3/1994 |
| JP | | 6114037 | 4/1994 |
| JP | | 6285044 | 10/1994 |
| JP | | 111985 | 5/1995 |
| JP | | 7289504 | 11/1995 |
| JP | | 08-248326 | 9/1996 |
| JP | | 11-142933 | 5/1999 |
| JP | | 2001-046358 | 2/2001 |
| JP | | 2001-091860 | 4/2001 |
| JP | | 2001-095755 | 4/2001 |
| JP | | 2001-095756 | 4/2001 |
| JP | | 2001-104241 | 4/2001 |
| JP | | 2001-104242 | 4/2001 |
| JP | | 2001-104243 | 4/2001 |
| JP | | 2001-104244 | 4/2001 |
| JP | | 2001-104287 | 4/2001 |
| JP | | 2001095756 A | * 4/2001 |
| JP | | 2001-137182 | 5/2001 |
| JP | | 2001-170002 | 6/2001 |
| JP | | 2001-174713 | 6/2001 |
| JP | | 2001-224551 | 8/2001 |
| JP | | 2001-224552 | 8/2001 |
| JP | | 2001-224553 | 8/2001 |
| JP | | 2001-231744 | 8/2001 |
| JP | | 2001-245844 | 9/2001 |
| JP | | 2005-003828 | 5/2005 |
| WO | | WO 98-11816 | 3/1998 |
| WO | | WO 00-22975 | 4/2000 |
| WO | | WO 00-76391 A1 | 12/2000 |
| WO | | WO 01-08548 | 2/2001 |
| WO | | WO 01-65995 | 9/2001 |
| WO | | WO 02-055126 | 7/2002 |
| WO | | WO 02-095351 | 11/2002 |
| WO | | WO 03/011103 | 2/2003 |
| WO | | WO 2004-035106 | 4/2004 |

OTHER PUBLICATIONS

U.S. Appl. No. 11/291,906, filed Dec. 2, 2005, Kislev et al.

BBC News Online—"Pill camera to 'broadcast from the gut'", Feb. 21, 2000, www.news.bbc.co.uk.

European Search Report of European Application 00937157.6, dated Feb. 13, 2004 .

European Search Report Application No. EP 05 02 6710 Dated Jan. 31, 2006.

European Search Report. Application No. EP 06022666. Date of completion of the search Dec. 4, 2006.

European Office Action Dated Nov. 16, 2006 Application 05026710.3.

European Office Action Dated Dec. 13, 2004 Application 00937157.6.

BR Japanese Office Action Dated Aug. 2, 2005 Application 2001-502738.

Japanese Office Action Dated Aug. 2, 2005 Application 2005-155953.

Katgraber F, Glenewinkel F, Fischler S, Int. J. Legal Med 1998; 111(3) 154-6.

Manual of Photogrammetry, Thompson (Ed.), Third Edition, vol. Two, American Society of Photogrammetry, 1966.

Office Communication for U.S. Appl. No. 10/009,837 Dated Oct. 2, 2003.

Office Communication for U.S. Appl. No. 10/009,837 Dated Oct. 28, 2003.

Office Communication for U.S. Appl. No. 10/009,837 Dated Apr. 30, 2004.

Office Communication for U.S. Appl. No. 10/879,276 Dated Dec. 14, 2004.

Office Communication for U.S. Appl. No. 11/115,320 Dated Mar. 30, 2006.

Office Communication for U.S. Appl. No. 11/115,320 Dated Oct. 13, 2006.

The Radio Pill, Rowlands, et al., British Communications and Electronics, Aug. 1960, pp. 598-601.

Wellesley company sends body monitors into space—Crum, Apr. 1998.

Wireless transmission of a color television moving image from the stomach using a miniature CCD camera, light source and microwave transmitter. Swain CP, Gong F, Mills TN. Gastrointest Endosc 1997;45:AB40.

Muretto et al., "An endogastric capsule for measuring tumor markers in gsatrict juice: an evaluation of the safety and efficacy of a new diagnostic tool" Jan. 2003.

Electronic Sputnik Capsule Against Parasites-Turner 2001.

European Search Report Application No. EP 07001478 Mailed Apr. 10, 2007.

Evans et al., Studies of the Human Gastro-Intestinal Tract in the Ambulatory Subject Using the Pressure Sensitive Radiotelemetry Capsule.

Yarbrough et al., Evaluation of the Heidelberg Ph Capsule, The American Journal of Surgery, vol. 117, Feb. 1969, pp. 185-192.

The Heidelburg pH Capsule System Telemetric Fasting Gastric Analysis.

International Search Report Application No. PCT/IL00/00349 Mailed Nov. 27, 2000.

Localization of a wireless capsule endoscope in the GI Tract, Gastrointestinal Endoscopy 2001; 53:AB126.

Nam et al., "A method for Position Detection of the wireless capsule endoscopes Module Using the Solution of Nonlinear Simultaneous Equations", Sensors Conference 2002, p. 377.

Notice of Allowance for U.S. Appl. No. 11/291,906 Mailed May 2, 2007.

Shin-ichi et al., Robots for the future, Nov. 29, 2001.

Transit times for the capsule Endoscope, Gastrointestinal Endoscopy 2001; 53:AB122.

Video Camera to "TAKE"—RF System Lab, Dec. 25, 2001.

Wang et al., "Integrated Micro-Instrumention for Dynamic Monitoring of the Gastro-intestinal Tract", Presented at IEEE Instrumentation for Dynamic Monitoring of the Gastro-Intestinal Tract, Presented at IEEE Instrumentation and Measurement Technology Confrence, May 2002, Anchorage, Ak, USA, www.see.ed.ac.uk/Naa.publications.html.

W. Weitschies R. Kotitz, D. Cordin, L. Trahms, High-Resolution Monitoring of the Gastrointestinal Transit of a Magnetically Marked Capsule (1997), Journal of Pharmaceutical Sciences, vol. 86, No. 11, pp. 1218-1222.

Weitschies et al., Magnetic marker monitoring of disintegrating capsule, European Journal of Pharmaceutical Sciences 13, 411-416, 2001.

Written Opinion of Application No. PCT/IL00/00349 Mailed on Apr. 13, 2001.

www.rfnorkia.com-NORIKA3, Dec. 24, 2001.

www.middleeasthealthmag.com- Review proves the value of computers, Nov. 29, 2001.

Office Communication of U.S. Appl. No. 11/115,320 Dated Apr. 30, 2007.

Office Action of U.S. Appl. No. 11/221,841 Dated Sep. 5, 2008.

Office Action of European Application No. 05026710.3-1265 Dated Jun. 2, 2008.

Office Action of U.S. Appl. No. 11/221,841 mailed on Feb. 20, 2009.

Office Action of U.S. Appl. No. 11/221,841, mailed on Aug. 28, 2009.

Final Office Action, issued Apr. 12, 2010, for U.S. Appl. No. 11/221,841.

Notice of Allowance, issued Jun. 9, 2010, for U.S. Appl. No. 11/221,841.

* cited by examiner

IN-VIVO IMAGING DEVICE, OPTICAL SYSTEM AND METHOD

CROSS REFERENCE TO RELATED APPLICATIONS

This application is a continuation-in-part of U.S. application Ser. No. 10/879,276 filed on 30 Jun. 2004, entitled "An Optical System" which in turn is a continuation-in-part of U.S. application Ser. No. 10/009,837 filed on 22 Aug. 2002, entitled "An Optical System", which is a national phase application of International Application PCT/IL00/00349 filed 15 Jun. 2000 and a continuation-in-part of U.S. application Ser. No. 10/478,252, filed on 20 Nov. 2003, entitled "A Method for In Vivo Imaging of an Unmodified Gastrointestinal Tract" which is a national phase application of International Application PCT/IL02/00391 filed 20 May 2002, all of which are incorporated in their entirety by reference herein. International Application PCT/IL00/00349 filed 15 Jun. 2000 claims benefit from Israeli Patent Application No. 130486 filed 15 Jun. 1999. International Application PCT/IL02/00391 filed 20 May 2002, claims benefit from Israeli Patent Application No. 143258 filed 20 May 2001.

FIELD OF THE INVENTION

The present invention relates to an in-vivo device for imaging; more specifically, to optical systems for such devices and methods for their use, and to in vivo imaging of lumens such as the gastrointestinal tract in unmodified conditions.

BACKGROUND OF THE INVENTION

An optical system for illuminating and viewing a target, which may include for example a target, a source of illumination of the target and an imager or other device for receiving the light remitted from the target, can be defined by or analyzed in light of, for example, an illumination axis and optical axis that may converge at the target.

Such an optical system may be as simple as an operator of an illumination source viewing a target, wherein the operator embodies the imager, and is the unit receiving the light remitted from the target. An example of such an optical system is an operator of a vehicle, inside the vehicle and looking out at an illuminated target such as a road or tunnel walls.

Other optical systems may include other components such as automated processors as imaging devices receiving the light remitted from a viewed target. Examples of such optical systems can be found in diagnostic apparatuses such as endoscope devices. The endoscopes described in the art may include, for example an image pickup element and an illuminating element for illuminating an examined target, and other components.

For some optical systems it may be advantageous to have the illuminating element and receiving element contained within a single compartment, for example behind a single optical window.

In devices typically used to view the gastrointestinal tract, such as endoscopes, when the device is inserted into the intestine the field of illumination may be obscured by folds of the intestine wall collapsing on the tip of the endoscope. This and other problems may be solved by insufflating air in the intestine. Air insufflation may inflate the intestinal walls, flatten the folds that are naturally present in the intestine wall, and remove potential obstruction from both the illumination source(s) and from the imager.

Air insufflation of the intestine may change the normal physiological conditions of the intestine. In an unmodified environment viewing conditions in the intestine may be similar to underwater viewing. Air insufflation may modify these conditions.

SUMMARY OF THE INVENTION

Embodiments of the present invention may include an in-vivo device, an optical system, and a method for viewing in-vivo sites.

A dome or cover may cover an end of the device, protecting optical elements such as illumination devices or imagers, which may be behind the dome. The dome may be forward projecting.

In one embodiment, an in-vivo imaging device includes a device body, having a longitudinal axis, an imager, and an optical system. The optical system may be positioned at a first end of the device, and the field of view of the imager may be forward looking, and/or may be via the optical system along the longitudinal axis and towards the first end.

In one embodiment, the device may illuminate and view a target in which device an illumination element and a receiving unit are disposed behind a single optical window or dome. Images may be obtained, for example, having reduced or no backscatter and stray light.

An optical system according to an embodiment of the present invention may include at least one illumination element and at least one receiving unit, both disposed behind a single-optical window. In prior art imaging devices, illumination units and imaging units may be behind separate windows.

In some embodiments, the optical window is configured such that it defines a shape having at least one focal curve. At least one illumination element and at least one receiving unit may be geometrically positioned (for example on the focal curve plane or in proximity of the focal curve plane) such that, when illuminating, rays from the illumination elements, some of which are internally reflected from the internal surface of the optical window, will not be incident on the receiving unit.

It will be appreciated that the terms "receiving unit" and "imaging unit" relate to any unit suitable for receiving, processing or further transmitting illumination rays remitted from a target or data derived from these rays. For example, an imager or camera, such as a Charge Coupled Device (CCD) camera or imager or a Complementary Metal Oxide Semiconductor (CMOS) imager or camera may be used; other suitable receiving or imaging units may be used.

In one embodiment of the invention the optical window may be an ellipsoid shaped dome. One or more illumination elements are positioned on the ellipsoid focal curve and a receiving unit is positioned on the axis of symmetry of the ellipsoid at an equal distance from the illumination elements. The components of such an embodiment, thus positioned, ensure that when illuminating, light internally reflected from the optical window surfaces is received at points on the focal curve and is not incident on the receiving unit.

Embodiments of the present invention include diagnostic instruments including an optical system according to the present invention.

Embodiments of the present invention may provide a simply assembled diagnostic device which can obtain data, essentially free of noise such as backscatter and stray light.

Further embodiments of the present invention include a method and device for in vivo imaging of body lumens such as the gastrointestinal tract in unmodified or largely unmodified conditions. Other lumens may be imaged.

According to one embodiment, the intestine or other lumens may be viewed through for example an optical dome, which may prevent for example obscuring of the field of illumination or of the field of view, due to collapse or due to a fold of the intestine wall. For example a device such as a capsule, an autonomous device, or an endoscope may include a projecting optical dome. According to an embodiment of the invention the optical dome may be convex shaped. For example, the dome may be an ellipsoid shaped dome, but may include other non-ellipsoid convex shapes.

A method according to one embodiment may include introducing into an uninsufflated lumen such as the intestine an imaging device and obtaining images. The imaging device may include, for example, a dome shaped or substantially convex end through which the area is illuminated and viewed.

In embodiments where illumination elements and a unit for receiving remitted light are contained behind a single optical window, "noise" (e.g., backscatter and stray light) produced by light remitted from the optical window itself may be reduced, and less of such noise may be received by the receiving unit.

BRIEF DESCRIPTION OF THE DRAWINGS

The present invention will be understood and appreciated more fully from the following detailed description taken in conjunction with the figures in which.

DETAILED DESCRIPTION OF THE INVENTION

Figure 1:
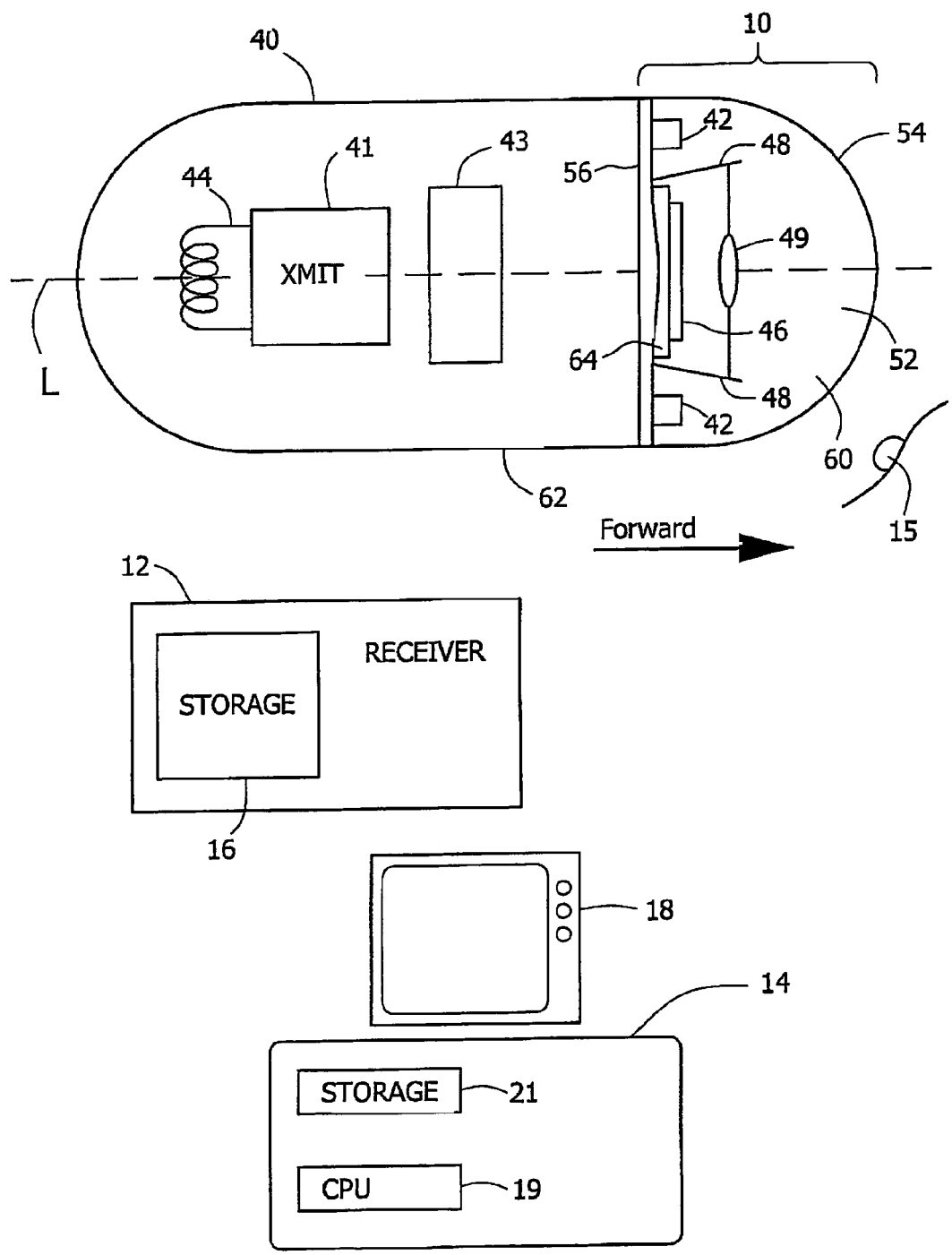
FIG. 1 is a schematic diagram of a device and system according to one embodiment of the present invention.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Embodiments of the present invention include an optical system which may geometrically position both illumination elements and units for receiving light behind a single optical window, dome, etc., such that internally reflected (e.g., by refraction) light from the optical window will not be incident on the receiving unit.

An optical window having a shape having focal points (for example, an ellipse) has the optical property that light rays emitted from one focal point of the shape, which are internally reflected, are propagated to the second focal point. In a three dimensional shape (such as an ellipsoid) light rays emitted from a point on a focal curve, which are internally reflected, will be propagated to another point on the focal curve.

For example, in the field of arc lamp systems this property is used to collect energy efficiently. For example in Model A-1010 and A-1010B lamp housings provided by Photon Technology International of New Jersey, U.S.A., an arc source is located at a foci of an ellipsoid reflector and the radiation is reflected to another foci. Energy is collected efficiently since the light is brought to a focus by reflection rather than by refraction (through a lens) such that there is no loss due to absorption or lens surface back reflection.

In the optical system of some embodiments of the present invention the illumination elements and imager are positioned within an optical dome such that illumination rays from the illumination source that are internally reflected from the optical window are not incident on the imager. For example, the illumination sources may be positioned on focal points and the imager's position does not coincide with the focal points, thus ensuring that internally reflected light is propagated to focal points and not received by the receiving unit. Other configurations are possible.

Some embodiments of the present invention may include imaging devices that may include a configuration which can allow imaging of an un-modified or un-insufflated lumen; in some contexts and with some uses such techniques may be referred to as "airless endoscopy".

Various embodiments of the invention need not include all the aspects discussed herein. For example, an in-vivo imaging device (e.g., an endoscope, a capsule, etc.) may include a protruding dome, but not include an arrangement for avoiding backscatter as disclosed herein.

A system according to some embodiments of the invention may include an in-vivo sensing device transmitting information (e.g., images or other data) to a data receiver and/or recorder possibly close to or worn on a subject. A data receiver and/or recorder may of course take other suitable configurations. The data receiver and/or recorder may transfer the received information to a larger computing device, such as a workstation or personal computer, where the data may be further analyzed, stored, and/or displayed to a user. In other embodiments, each of the various components need not be required; for example, an internal device may transmit or otherwise transfer (e.g., by wire) information directly to a viewing or processing system. While in one embodiment the device is an autonomous capsule, other configurations, such as an endoscope or trocar may be used.

Reference is made to FIG. 1, which is a schematic diagram of a device and system according to one embodiment of the present invention. In one embodiment, the system may comprise an imaging device, such as for example a device 40 which may, for example, be capsule shaped, optical system 10 including, for example, optical window 54, lens 49, baffle or separator 48, imager 46 or other receiving unit, one or more illumination source(s) 42, and one or more power source(s) 43. Power source(s) 43 may be, for example, a suitable battery, but in further embodiments may be other devices, such as a unit for receiving power from an external source, etc. Optical system 10 is described in more detail below. Optical window 54 typically defines a space 52 behind which sits optical components such as imager 46, baffle 48, lens 49, and illumination source(s) 42. For example, if the empty areas inside device 40 include common air rather than a specialized isolated gas, space 52 may be an air space. Baffle or separator 48 may provide additional functionality, such as holding other components. For example baffle 48 may act as a lens holder. Baffle or separator 48 may help to optically isolate imager 46 and illumination source(s) 42. Typically, the imager 46 images via optical window 54 and illumination source(s) 42 illuminate via optical window 54.

Imager 46 may be fixed or otherwise attached to a substrate such as circuit board 64. Circuit board 64 is typically further attached to a substrate 56, which may for example support illumination source(s) 42 (which may be supported by its/their own substrate or circuit board, which may be supported by or integrated with substrate 56) and which may define a forward area 60 of device 40. Optical window 54 may form space 52 by, for example, connecting with circuit board 64. In one embodiment, imager 46 is within space 52 and at least some imaging portions of the imager 46 are not in contact with the optical window 54 but rather touch air in the space 52. Circuit board 64 may be any suitable substrate, such as a circuit board, a plastic sheet or plate, etc. Device 40 may include a transmitter 41 (typically operating wirelessly via radio waves), and an antenna 44, for transmitting images and possibly other information to, for example, a receiving device. Other types of transmitters and transmission methods may be used; for example, in an endoscopic application, wire or other transmission may be used. Typically, the imaging device may correspond to embodiments described in U.S. Pat. No. 5,604,531 to Iddan et al., and/or to embodiments described in published application WO01/65995 to Glukhovsky et al., both of which are incorporated herein by reference in their entirety, but in alternate embodiments there may be other types of imaging devices. In one embodiment, an imaging device may include more than one image sensor. Device 40, and other devices disclosed herein, may be used to view lumens such as the gastrointestinal tract in an unmodified form, not using techniques such as insufflation.

Typically, located outside the patient's body in one or more locations may be an image receiver 12, a data processor 14, and an image monitor 18. Image receiver 12 may include an image receiver storage unit 16. Data processor 14 may include a processor 19 and a storage unit 21.

Optical window 54 is in one embodiment convex or substantially convex and smooth, and projects outward from the main body 62 of device 40 in a "forward" direction, although note that "forward" is a relative term, as in some embodiments in use the imaging section of device 40 may either lead or follow the rest of the device 40 as it traverses a body lumen. For example, the device 40 may, depending on circumstance, traverse a lumen such that the imager 46 faces forward or backward, as device 40 may be designed so that there are two possible directions of travel, both parallel to the axis L of device 40. The direction of travel need not be parallel to the longitudinal axis L, and other configurations (e.g., spherical) may be used. In an embodiment where the device 40 has one or two possible directions of travel (e.g., forward, or forward and backward), the forward end may be defined as being at the end of the device in which the device travels, or one of such ends. In one embodiment, the field of view of the imager 46 via the optical system is along the longitudinal axis L and towards the "front" end; objects generally beyond the "front" end, such as target or object 15, are imaged. Optical window 54 may be ellipsoid shaped, but may include other non-ellipsoid convex shapes.

Optical window 54 is typically transparent, or includes a transparent window or portion. Optical window 54 typically provides one uninterrupted field of view for optical components. The optical dome 54 may in some embodiments project from the main body 62 of the device (possibly in a smooth contoured manner, and may be integral with the main body 62), and thus may lead or follow the device through a lumen, depending on the direction of travel. The optical dome 54 is preferably made of plastic, glass or other suitable material. Typically, the area to be viewed is illuminated and viewed through the optical dome 54, and thus optical components such as the imager 46 and illumination elements are behind the dome, within the device 40. Typically, optical window 54 in combination with the main body 62 provides a relatively smooth and streamlined body as it traverses a body lumen. Typically, at least one end of the device 40 is substantially convex; for example optical window 54 may be considered a convex forward projecting or protruding end of device 40. The window 54 typically protrudes relative to a direction of travel of the device 40. The device 40 typically collects images of objects which are located generally forward of the forward end of the device 40 (or backward if the device 40 is moving backwards), typically up to a 140 degree angle of view although other angles may be used.

Main body 62 may be in some embodiments the tube of an endoscope or trocar, and thus may extend further rearward than as depicted in the device 40 of FIG. 1. Further, more than one optical system may be included in a device such as device 40. For example, a device similar to embodiments described in U.S. application Ser. No. 10/046,541 filed on 16 Jan., 2002 which is, incorporated by reference in its entirety, may include optical systems as described herein.

Imager 46 may include, for example, a CCD camera or imager, a CMOS camera or imager, a digital camera, a still camera, a video camera, or other suitable one or more imagers, cameras, receiving units or image acquisition components.

Device 40 typically may be or may include an autonomous swallowable capsule, which is self contained, but device 40 may have other shapes and need not be swallowable or autonomous (e.g., device 40 may have other configurations, such as that of an endoscope or trocar). In one embodiment, device 40 is shaped such that its eccentricity is equal to or larger than zero and smaller than 1. Device 40 may be a capsule or other unit where all the components are substantially contained within a container or shell, and where device 40 does not require any wires or cables to, for example, receive power or transmit information. In one embodiment, all of the components may be sealed within the device body (the body or shell may include more than one piece); for example, an imager, illumination units, power units, and transmitting and control units, may all be sealed within the device body. Device 40 may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Transmitter 41 includes control capability for, for example controlling the various operations of device 40, although control capability or one or more aspects of control may be included in a separate component. Transmitter 41 is typically an ASIC (application specific integrated circuit), but may be of other constructions; for example, transmitter 41 may be a processor executing instructions. Device 40 may include a processing unit separate from transmitter 41 that may, for example, contain or process instructions.

Typically, located outside the patient's body in one or more locations may be an image receiver 12, a data processor 14, and an image monitor 18. Image receiver 12 may typically include an antenna or antenna array and an image receiver storage unit 16. Data processor 14 may include a processor 19 and a storage unit 21. Image monitor 18 may display, inter alia, images recorded by, for example, device 40. Typically, data processor 14 and monitor 18 may be part of a personal computer or workstation, which includes standard components such as processor 19, a memory, a disk drive, and input-output devices, although alternate configurations are possible. Data processor 14 may typically, as part of its functionality, act as a controller controlling the display of the images. Image monitor 18 may typically be a conventional video display, but may, in addition, be any other device capable of providing images or other data and may be of any size monitor including large projection size monitors. The image monitor 18 presents the image data, typically in the form of still and streaming image frames, and in addition may present other information. In an exemplary embodiment, the various categories of information are displayed in windows. Other displaying formats may be used.

In operation, imager 46 may capture images and may send data representing the images to transmitter 41, which may transmit data to image receiver 12 using, for example, electromagnetic radio waves. Image receiver 12 may transfer the image data to image receiver storage unit 16. After a certain period of time of data collection, the image data stored in storage unit 16 may be transferred to the data processor 14 or the data processor storage unit 21. For example, the image receiver 12 or image receiver storage unit 16 may be taken off the patient's body and may be connected to a personal computer or workstation that may include the data processor 14 via a standard data link, e.g., a serial, parallel, USB, or wireless interface. According to one embodiment the image data may then be transferred from the image receiver storage unit 16 to data processor storage unit 21. Data processor 14, including possibly dedicated software, may analyze the data and provide the analyzed data to the image monitor 18, where a user views the image data. Other configurations allow for real time viewing. Further, other methods of recording, transmitting, storing and viewing images recorded by imager 46 may be used.

Figure 2:
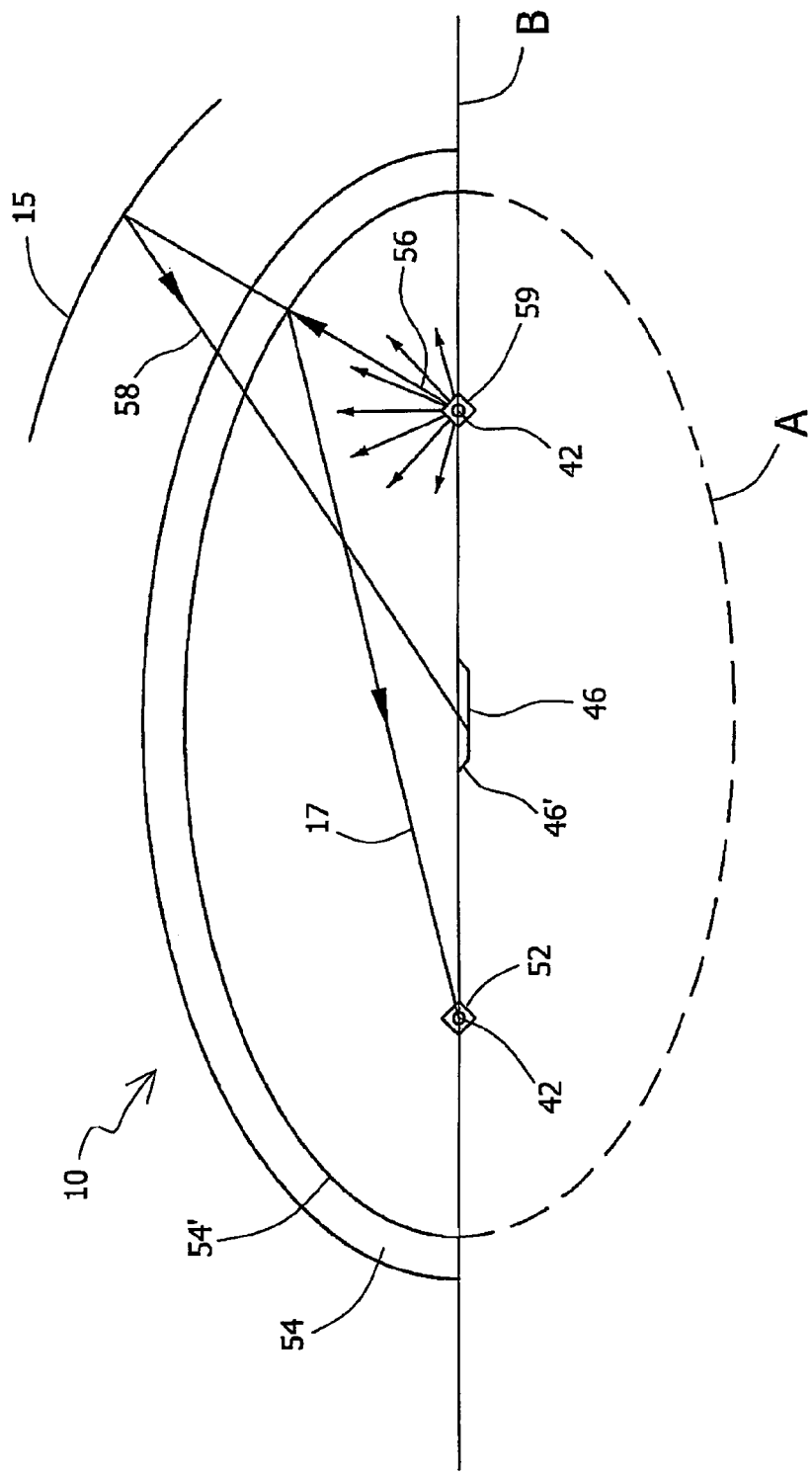
FIGS. 2 and 3 are schematic illustrations of an optical system according to embodiments of the present invention.

Reference is now made to FIG. 2, a schematic two dimensional presentation of an optical system according to an embodiment of the present invention. Referring to FIG. 2, optical system generally referenced 10 may be included in, for example, device 40 of FIG. 1, but may be included in other suitable devices, such as an endoscope, trocar, or other in-vivo imaging device. Optical system 10 may include, for example, illumination source(s) 42 and imager 46, disposed behind an optical window 54, for viewing target or object 15. Optical window 54 may have a surface configured such that a shape defined by it and by broken line A has an axis of symmetry B and, when viewed in cross section, two focal points 59 and 52. When viewed in three dimensions, a ring of focal points including focal points 59 and 52 may form a circle lying in a focal plane. Illumination source(s) 42 is positioned on focal point 59 and possibly other focal points and imager 46 is positioned on the axis of symmetry B not coinciding with either focal point 59 or 52 or other focal points.

The course of light rays emitted from illumination sources 42 will be followed as an example of the behavior of illumination rays in the optical system according to embodiments of the invention. Light 56 is emitted from an illumination source 42 (which element's position coincides with focal point 59) for illuminating target 15. A certain percent of the light (represented by ray 17) is internally reflected (typically via refraction) from the optical window 54 internal surface 54' and is propagated to the second focal point 52. A percent of the light 56 (represented by ray 58) is incident on target 15 (e.g., an object or area in-vivo), is reflected from target 15 and received by imager 46.

Thus, internally reflected light rays (such as ray 17) are propagated to areas outside the imager 46 area.

Imager 46 may also be unexposed to direct illumination from illumination sources 42; direct light from the illumination sources 42 is generally not incident on the imager 46. Illumination sources 42 may illuminate light 56 in a circular band that is tangent to line B. In this case, if imager 46 is positioned on line B it does not receive any direct illumination rays from illumination sources 42. Alternatively, imager 46 can be concealed in a niche 46', or surrounded or protected by for example a baffle or other structure, to avoid receiving direct illumination rays from illumination sources 42.

Thus, geometric positioning of the components of the system ensures that no or minimized backscatter, such as ray 17, and no or minimized direct light, only incident light, such as ray 58, is received by imager 46.

In actuality, the optical window 54 is a three dimensional shape. A three dimensional representation of the optical system 10 of FIG. 2, according to one embodiment, is shown in FIG. 3.

Figure 3:
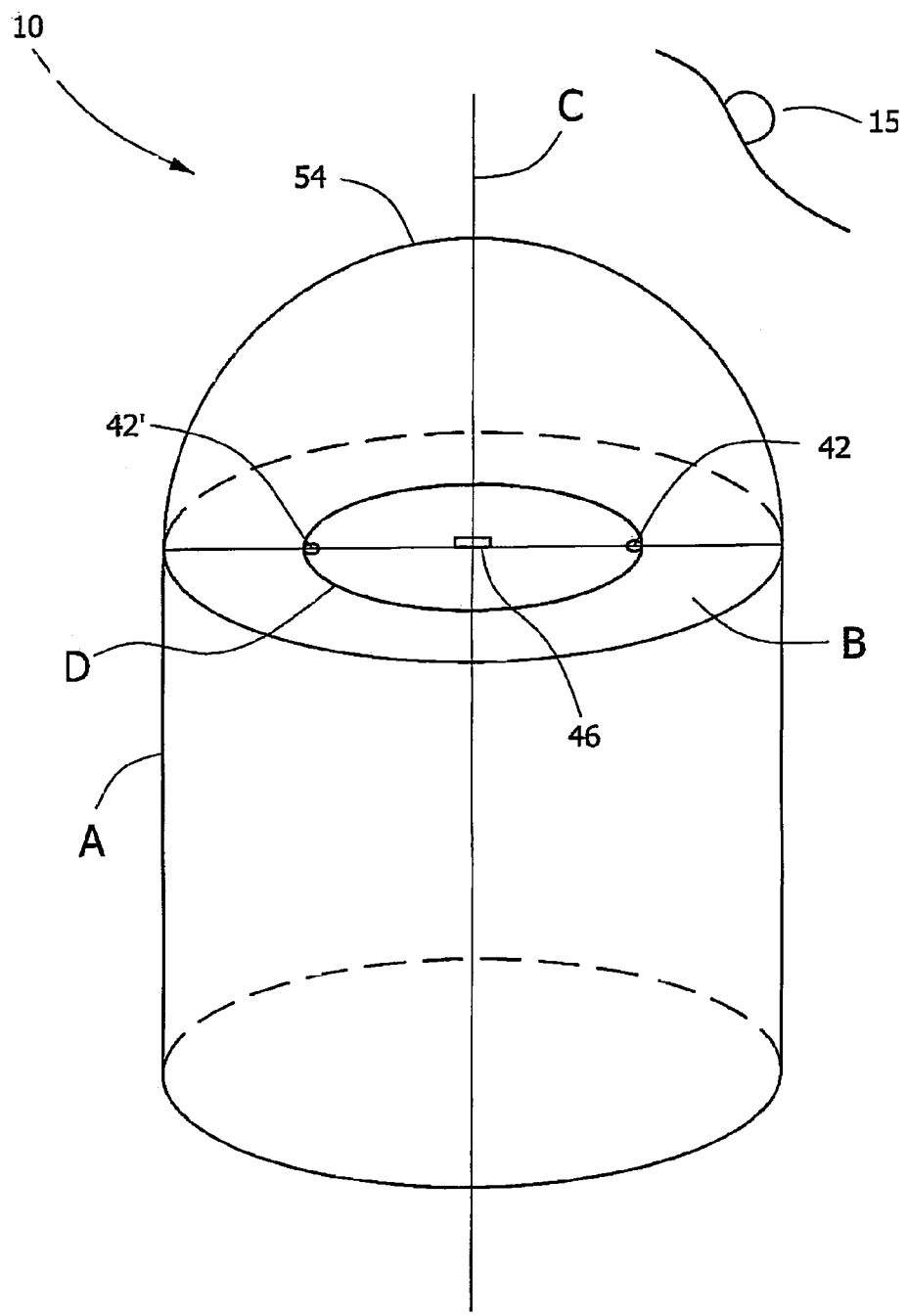

In the optical system 10 shown in FIG. 3 plane B, formed along line B from FIG. 2 is shown. Axis C is perpendicular to plane B. The shape on plane B which is defined by optical window 54, encompasses focal curve D. In other embodiments other arrangements and shapes for focal points, a focal curve, and a plane on which a focal curve lies, may be used.

One or more illumination elements, such as 42 and 42', may be positioned on focal curve D to, for example, help enable a uniform spatial illumination or to produce other results, though it should be appreciated that any suitable number of illuminating elements can be used according to specific requirements of the system.

In the arrangement shown, imager 46 is positioned at a point which is on, or in the vicinity of, axis C, essentially at an equal distance from both illumination source(s) 42 and 42', and on, or in the vicinity of, plane B, such that it receives incident light remitted from target 15. Other arrangements are possible. All or most of the light radiated from illumination source(s) 42 and 42' that is internally reflected from the optical window surfaces is received at points on focal curve D and is not incident on imager 46.

Thus, in one embodiment, data obtained by imager 46 is essentially free of backscatter and stray light.

Figure 4:
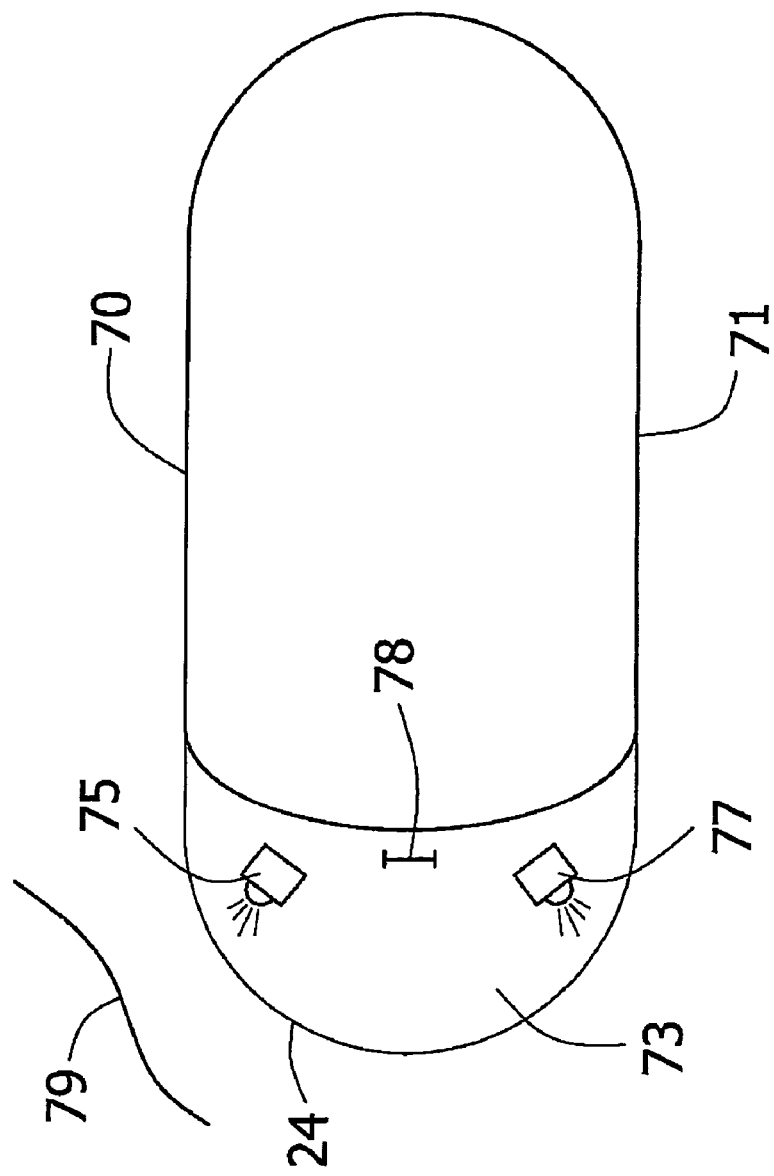
FIG. 4 is a schematic illustration of an in vivo imaging device according to an embodiment of the present invention.

FIG. 4 is an illustration of one embodiment of a swallowable device such as a capsule which includes, inter alia, a camera system, an optical system for imaging an area of interest onto the camera system and a transmitter which transmits the video output of the camera system. Other components, such as for example those depicted with respect to device 40 of FIG. 1, may also be included. The swallowable device depicted is a variant of embodiments disclosed in U.S. Pat. No. 5,604,531, assigned to the common assignees of the present application, which is hereby incorporated by reference. The device can pass through the entire digestive tract and thus may operate as an autonomous video endoscope.

In one embodiment, the device, generally referenced 70, is shaped as an ellipsoid; other suitable shapes may be used. The device 70 includes, for example, a housing unit 71 and a viewing unit 73, for viewing a target point 79 on for example the digestive tract wall. The viewing unit 73 includes, for example, an optical system.

The optical system may include, for example, a protective optical window 24, preferably made of plastic such as isoplast or other suitable material such as other plastics, glass, etc., one or more illumination elements 75 and 77 and an imaging device 78. Illumination elements 75 and 77 may be positioned on a focal plane perpendicular to the axis of symmetry of the ellipsoid defined by the body of the device 70. The imaging device 78, such as a camera, may be positioned on the axis of symmetry of the device 70.

Light rays emitted from illumination elements 75 and 77 that reach a target point 79 on the digestive tract wall are reflected to imaging device 78, whereas light rays internally reflected from protective optical window 74 may be propagated to points on the focal curve and not to imaging device 78.

Typically, the optical window 74 or the optical dome is one piece of plastic or glass or other suitable material, which is fixed to the overall device and is disposed of with the device. However, in other embodiments, the optical window or dome may be more than one unit, and need not be a separate unit from the rest of the shell for the device. In addition, in one embodiment, since protective optical window 74 is a single and complete unit, it is easily disposable, and can be smoothly replaced between different passes through the digestive tract. This fact, which is not affordable by endoscopes described in the art, may contribute to the sterile and facile use of a diagnostic device.

Figure 5:
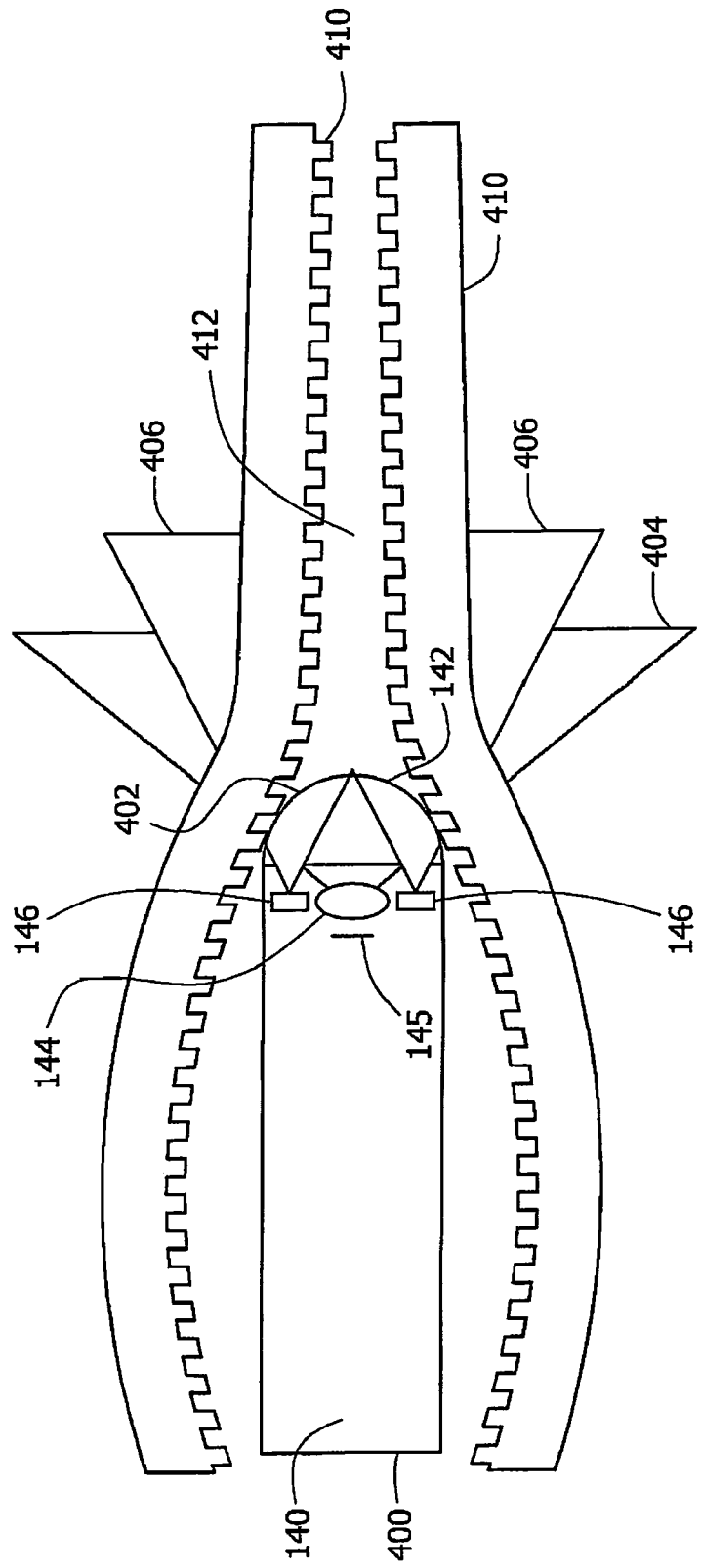
FIG. 5 is a schematic illustration of an in vivo imaging device according to an embodiment of the present invention.

Reference is now made to FIG. 5, which presents a schematic illustration of an in vivo imaging device which may be used to view lumens such as the gastrointestinal tract, according to an embodiment of the present invention. Endoscope 400 may image lumens in an unmodified environment, but modification may be used as well. Endoscope 400 includes an in vivo imaging device 140 and may be capable of being inserted and moved through for example the intestine; other lumens may be imaged. The in vivo imaging device 140 may be a subsection, portion, or attachment within or on device 400, and may share a structure and operation with, for example, device 40 above, but overall device 400 may have a structure and use similar to an endoscope. The dome or convex shaped tip 402 of endoscope 400 may include an optical window 142 through which the intestine is illuminated and viewed and/or imaged. Tip 402 or a portion thereof, such as window 142, may be substantially transparent, and may present a forward projecting convex portion. Optical window 142 may be similar to optical window 54, described above; however, other suitable optical windows or domes may be used. One or more illumination sources 146, an imager 145 and a lens 144 may be positioned behind optical window 142.

The collapsed, uninsufflated intestine walls 410 are in close proximity to the imaging device 140 and present only a limited area 412 to be viewed. In these conditions the field of view 404 may include the entire area 412. Furthermore, illumination field (or fields) 406 provided by illumination sources 146 may illuminate the entire area 412. When viewing, for example, the intestine, a limited area of the intestine wall may be fully illuminated and can be viewed in its entirety. Other configurations for illumination fields or view fields may be used. Other numbers of illumination devices may be used.

Figure 6:
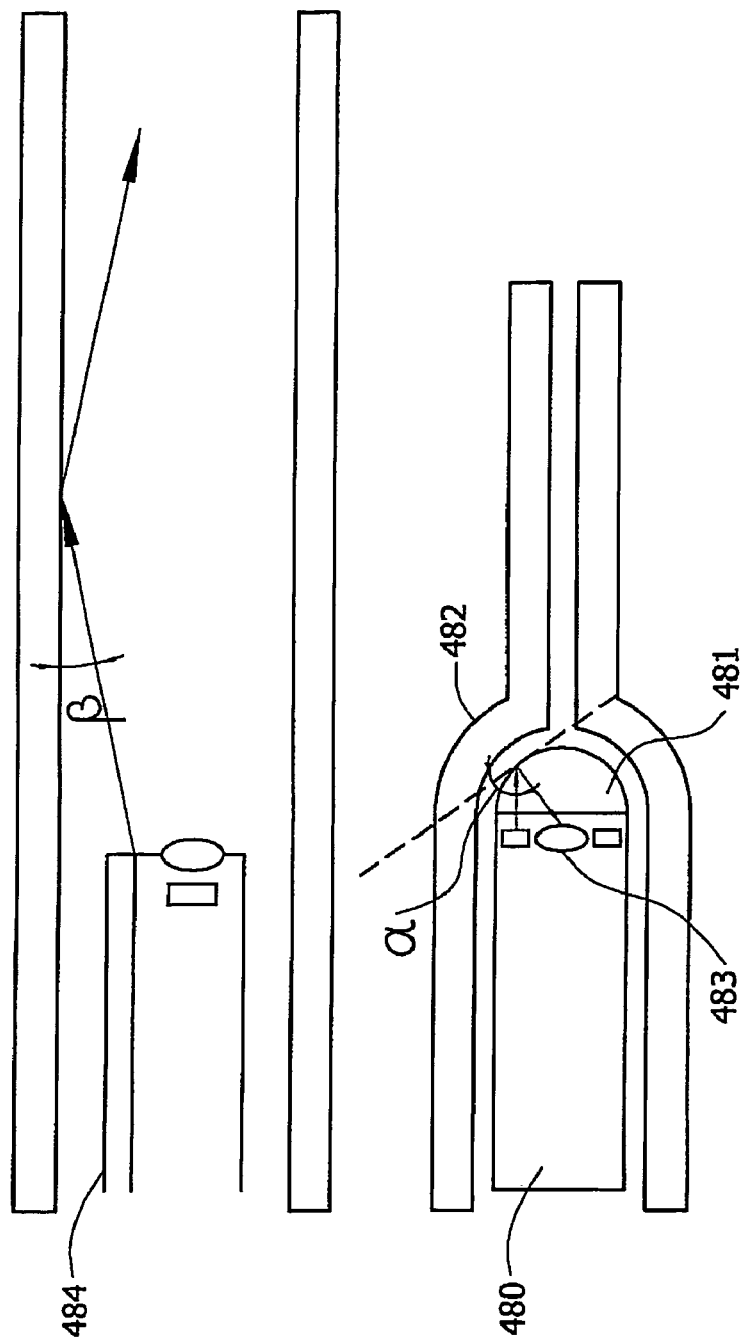
FIG. 6 is a depiction of an embodiment of the invention as compared to a prior art system.

FIG. 6 is a depiction of an embodiment of the invention as compared, for example, to a prior art system. Referring to FIG. 6, imaging device 480 may be a capsule, an endoscope or a portion of an endoscope, or another device, and may be structured and operated according to embodiments described herein. The illumination efficiency of imaging device 480 may be higher than that of prior art imaging device 484, for example due to the configuration of the end 481 of device 480, and also possibly because the lumen 482 is not insufflated. According to other embodiments insufflation may be used, and other benefits are possible. Illumination angle α is not as sharp an angle compared with sharp illumination angle β, such that most of the illumination is efficient and is returned from the intestine wall back to the imaging device and lens 483.

Figure 7:
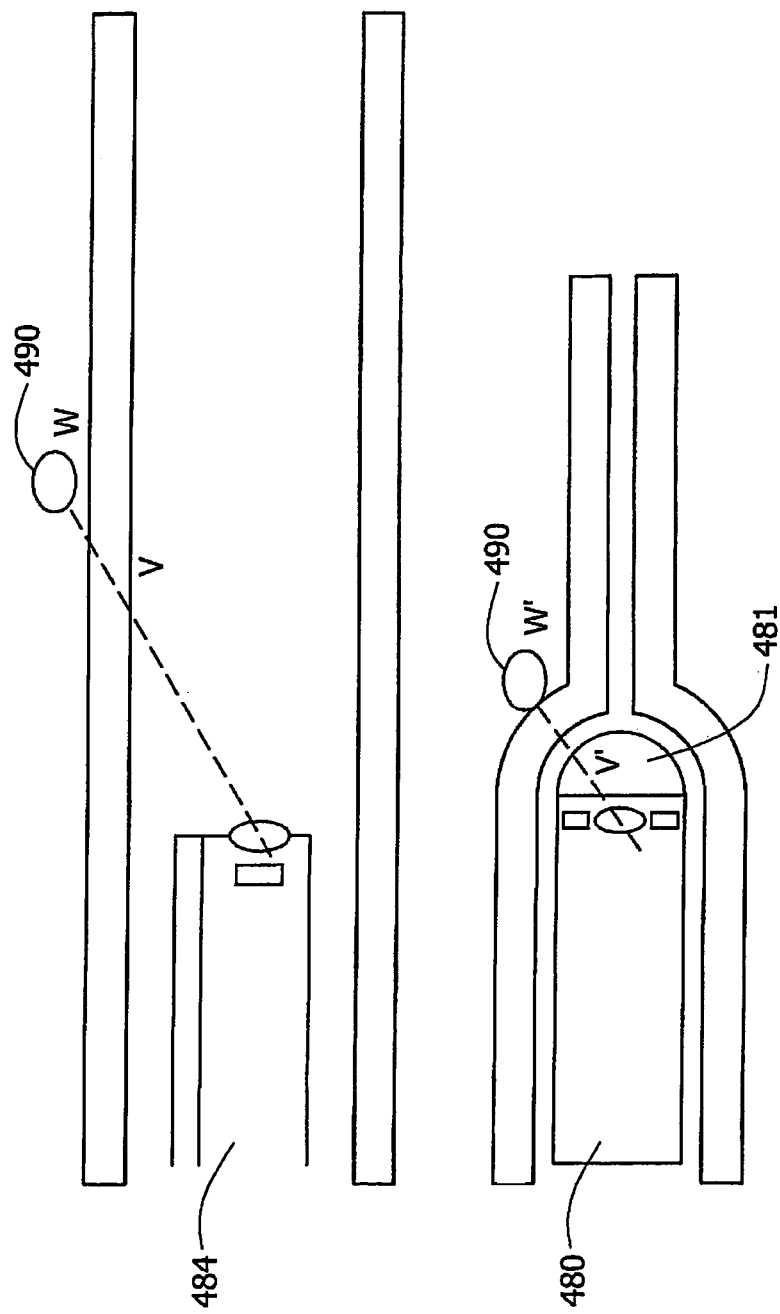
FIG. 7 is a depiction of an embodiment of the invention as compared to a prior art system.

FIG. 7 is a depiction of an embodiment of the invention as compared, for example, to a prior art system. As shown in FIG. 7, in some embodiments, the viewing angle of device 480 may be less sharp than the viewing angle of prior art imaging device 484. Formations such as arterioles, venulas, lymphatic ducts and others, which are located submucosively and which are viewed according to an embodiment of the invention, may be viewed through a thinner layer of mucosa than while being viewed by prior art imaging device 484. The optical path to the submucosal formation 490 is shorter (see distance v'–w') when using an imaging device 480 in accordance with an embodiment of the invention than when using a prior art imaging device 484 (see distance v–w). Other benefits are possible, and other configurations of a device according to an embodiment of the invention are possible.

As can be seen in FIGS. 6 and 7, the spatial resolution of the viewing may be improved when using an embodiment of the present invention. One cause, in some embodiments, may be that insufflation causes the intestine to be relatively cylindrically shaped. In a non-insufflated lumen and when using a device according to some embodiments described herein, collapsed walls of the intestine may form a half-sphere around end 481 (which may include the optical dome) of the device 480. Typically, the radius of the half sphere formed by the collapsed intestine walls is smaller than the radius of the cylindrical shape formed by insufflated intestine walls.

Figure 8:
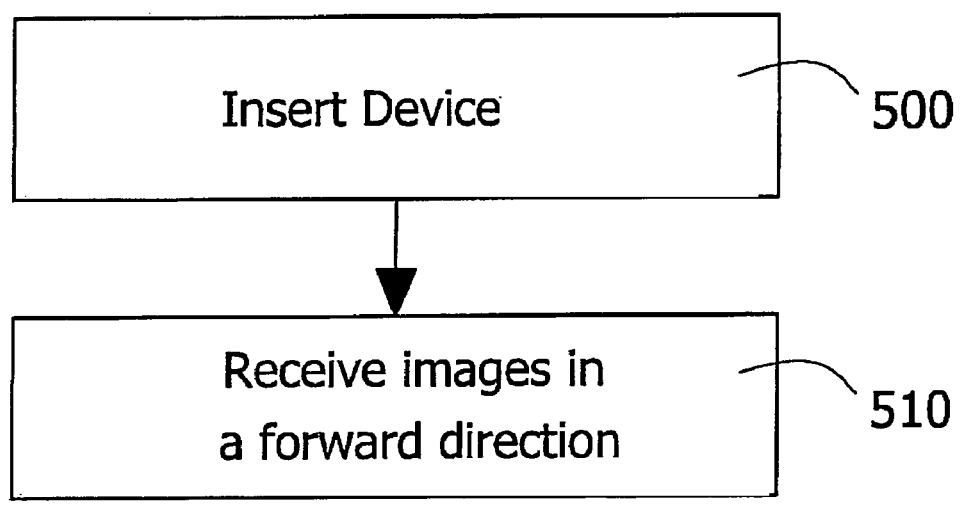
FIG. 8 is a flowchart depicting a method according to an embodiment of the present invention.

FIG. 8 is a flowchart depicting a method according to an embodiment of the present invention. Referring to FIG. 8, in step 500, a device is inserted into a body lumen (e.g., by swallowing, inserting by aid of an endoscope, etc.). In step 510, images are received at an imager within the device, the imager generally being forward looking (if the device happens to traverse the lumen in a backward direction, the imager may be backward looking). The forward direction may be substantially parallel to the longitudinal axis of the device. The device may be a device similar to those depicted in embodiments herein; however, other suitable devices may be used. For example images may be taken through a substantially convex forward. Other operations or series of operations may be used.

It will be appreciated by persons skilled in the art that the present invention is not limited to what has been particularly shown and described hereinabove. Alternate embodiments are contemplated which fall within the scope of the invention. In addition, aspects of the various embodiments disclosed herein are combinable with the other embodiments disclosed herein.

The invention claimed is:
1. An autonomous in-vivo imaging device comprising:
 a device body, the device body having a longitudinal axis and a main body, wherein a portion of the main body is parallel to the longitudinal axis and wherein an end of said parallel portion defines a plane perpendicular to the longitudinal axis;
 a dome shaped window positioned at said end of the parallel portion and defining a space between said dome shaped window and said plane, the dome shaped window having an uninterrupted transparent body that extends to said parallel portion of the main body of the device body;
 a plurality of illumination sources providing illumination through the window;
 a lens; and a camera positioned within the device body on an axis of symmetry coinciding with the longitudinal axis of the device at an equal distance from each of said plurality of illumination sources and behind the lens, the camera imaging via the lens and the window, the field of view of the camera via the lens being along the longitudinal axis and towards the end of the parallel portion, wherein said camera, lens and illumination sources are located behind said space.

2. The device of claim 1, wherein the device is a capsule.

3. The device of claim 1, wherein the device travels in at least a forward direction, and wherein the camera is forward looking.

4. A method for in-vivo imaging, the method comprising:
illuminating with a plurality of illumination sources disposed within a capsule, the capsule having a capsule body, the capsule body having a longitudinal axis and a main body, wherein a camera is positioned on an axis of symmetry coinciding with the longitudinal axis of the capsule at an equal distance from each of said plurality of illumination sources, wherein a portion of the main body is parallel to the longitudinal axis and wherein an end of said parallel portion defines a plane perpendicular to the longitudinal axis; and
receiving images at said camera from a forward direction via a lens, the forward direction being substantially parallel to the longitudinal axis of the capsule,
wherein the camera and illumination sources are covered by a convex dome shaped window positioned at said end of the parallel portion and defining a space between said dome shaped window and said plane, the window having an uninterrupted transparent body that extends to said parallel portion of the main body of the device body, the camera receiving images via the window and the illumination sources illuminating via the window, wherein said camera, lens and illumination sources are located behind said space.

5. The method of claim 4, wherein the device is autonomous.

6. The method of claim 4, wherein the dome shaped window extends from the main body in the direction of travel.

7. An in-vivo imaging device comprising:
a device body, the device body having a longitudinal axis and a main body, wherein a portion of the main body is parallel to the longitudinal axis and wherein an end of said parallel portion defines a plane perpendicular to the longitudinal axis;
a convex dome shaped window positioned at said end of the parallel portion and defining a space between said dome shaped window and said plane, the dome shaped window having an uninterrupted transparent body that extends to said parallel portion of the main body of the device body;
a camera imaging via a lens; and
a plurality of illumination sources, wherein said camera is positioned on an axis of symmetry coinciding with the longitudinal axis of the device at an equal distance from each of said plurality of illumination sources, the camera and the illumination sources being behind the dome shaped window, the camera accepting images via the dome shaped window, wherein said camera, lens and illumination sources are located behind said space.

8. The device of claim 7, wherein the device is autonomous.

9. The device of claim 7, wherein the device is a capsule.

10. The device of claim 7, wherein the device travels in at least a forward direction, and wherein the camera is forward looking.

11. The device of claim 7, wherein the illumination source illuminates through the dome shaped window.

12. The device of claim 7, wherein the dome shaped window is ellipsoid shaped.

13. An in-vivo imaging device comprising:
a device body, the device body having a longitudinal axis and a main body, wherein a portion of the main body is parallel to the longitudinal axis and wherein an end of said parallel portion defines a plane perpendicular to the longitudinal axis;
plurality of illumination sources;
a camera positioned behind a lens and on an axis of symmetry coinciding with the longitudinal axis of the device at an equal distance from each of said plurality of illumination sources; and
a window being substantially dome-shaped positioned at said end of the parallel portion and defining a space between said window and said plane, said window having an uninterrupted transparent body that extends to said parallel portion of the main body of the device body, the camera accepting images via the window and the illumination source illuminating via the window, wherein said camera, lens and illumination sources are located behind said space.

14. The device of claim 13, wherein the device is autonomous.

15. The device of claim 13, wherein the device is a capsule.

16. The device of claim 13, wherein the window projects from the main body of the device.

17. An in-vivo imaging method comprising:
collecting images via a camera imaging via a lens, the camera being in a device having a device body, the device body having a longitudinal axis and a main body, wherein a portion of the main body is parallel to the longitudinal axis and wherein an end of said parallel portion defines a plane perpendicular to the longitudinal axis, the device having a window which is substantially convex, the window positioned at said end of the parallel portion and defining a space between said window and said plane, the window having an uninterrupted transparent body that extends to said parallel portion of the main body of the device body, the camera accepting images via the window, the device having a plurality of illumination sources illuminating via the window, wherein the camera is positioned on an axis of symmetry coinciding with the longitudinal axis of the device at an equal distance from each of said plurality of illumination sources, wherein said camera, lens and illumination sources are located behind said space.

18. The method of claim 17, comprising collecting images of objects in a generally forward direction from the end of the device.

19. The method of claim 17, comprising transmitting the images wirelessly.

20. The method of claim 17, wherein the device is a capsule.

21. An in vivo imaging capsule comprising:
a capsule housing, said capsule housing having a longitudinal axis and a main housing, wherein a portion of the main housing is parallel to the longitudinal axis and wherein an end of said parallel portion defines a plane perpendicular to the longitudinal axis;
at least a camera imaging via a lens; and
a plurality of illumination sources;

the lens and illumination sources being on a plane substantially at right angle with the longitudinal axis and coinciding with or behind said plane defined by the end of said parallel portion, wherein said camera and lens is positioned on an axis of symmetry coinciding with the longitudinal axis of the capsule at an equal distance from each of said plurality of illumination sources;

wherein said main housing is attached to a convex dome shaped window positioned at said end of the parallel portion and defining a space between said dome shaped window and said plane, the dome shaped window having an uninterrupted transparent surface that extends to said parallel portion of the main housing of the capsule housing, the camera imaging via the dome shaped window and the illumination sources providing illumination through the dome shaped window.

* * * * *